_(12)_ United States Patent
Clauss

(10) Patent No.: US 7,468,163 B2
(45) Date of Patent: Dec. 23, 2008

(54) RECEPTION HEAD FOR A FILTER UNIT

(75) Inventor: Christian Clauss, Obernai (FR)

(73) Assignee: Millipore Corporation, Billerica, MA (US)

( * ) Notice: Subject to any disclaimer, the term of this patent is extended or adjusted under 35 U.S.C. 154(b) by 439 days.

(21) Appl. No.: 10/525,430

(22) PCT Filed: Oct. 24, 2003

(86) PCT No.: PCT/IB03/05110

§ 371 (c)(1),
(2), (4) Date: Feb. 23, 2005

(87) PCT Pub. No.: WO2004/037380

PCT Pub. Date: May 6, 2004

(65) Prior Publication Data

US 2005/0233436 A1 Oct. 20, 2005

(30) Foreign Application Priority Data

Oct. 28, 2002 (FR) ................................ 02 13483

(51) Int. Cl.
*B01D 35/00* (2006.01)
*B01D 35/30* (2006.01)
*B01D 29/00* (2006.01)

(52) U.S. Cl. .................. 422/101; 422/104; 210/232; 210/406; 210/433.2; 210/445; 210/451

(58) Field of Classification Search ............... None
See application file for complete search history.

(56) References Cited

U.S. PATENT DOCUMENTS 4,678,576 A * 7/1987 Leoncavallo .......... 210/321.87
5,092,988 A 3/1992 Womack et al.
5,096,588 A 3/1992 Alberson
5,172,332 A 12/1992 Hungerford et al.
5,234,585 A * 8/1993 Zuk, Jr. ..................... 210/188
5,306,420 A 4/1994 Bisconte
6,027,638 A * 2/2000 Johnson .................... 210/86
6,133,045 A 10/2000 Chen et al.
6,171,480 B1 1/2001 Lee et al.
6,358,730 B1 3/2002 Kane
6,884,341 B2 * 4/2005 Ferguson .................. 210/132
6,905,594 B2 * 6/2005 Ferguson .................... 210/90
7,067,055 B2 6/2006 Ruppel
2004/0000518 A1 1/2004 Haley, III

FOREIGN PATENT DOCUMENTS

WO WO 01/48141 A1 7/2001
WO WO 02/068580 A2 9/2002

OTHER PUBLICATIONS

International Search Report dated Feb. 27, 2004.

* cited by examiner

*Primary Examiner*—Krishnan S Menon

(57) ABSTRACT

The invention relates to a mechanical support for a drainage device of a filter unit for microbiological testing of liquid substances. Said filter unit is provided with a membrane and adapted to be mounted on said mechanical support so that said membrane faces a reception surface of said mechanical support. The mechanical support comprises: a passage one end of which discharges externally of said reception surface and the other end of which discharges internally said reception surface; and selectively operable means for closing said passage, movable between a first position in which they close said passage and a second position in which they open said passage.

13 Claims, 3 Drawing Sheets

RECEPTION HEAD FOR A FILTER UNIT

CROSS REFERENCE TO RELATED APPLICATIONS

This application is the U.S. National Stage Application of International Application No.: PCT/2003/005110, filed on Oct. 24, 2003, which claims priority to French Application No.: 0213483, filed on Oct. 28, 2002.

The present invention relates to a mechanical support for a drainage device of a filter unit for microbiological testing of liquid substances.

Said filter unit is provided with a membrane on which the microorganisms contained in the liquid substance are concentrated during drainage.

The membrane is then placed in an agar culture medium to encourage the growth of said microorganisms.

There are prior art drainage devices which avoid contaminating a liquid substance to be analyzed by forcing a sample of the liquid substance through a membrane by creating a reduced pressure on the downstream side of the membrane.

In devices of the above kind a vacuum pump is generally connected to a flask to create a reduced pressure therein and a receptacle closed at the bottom by said membrane is mounted directly on the flask. Thanks to the suction induced by the reduced pressure, the liquid substance sample contained in said receptacle is aspirated into the flask and the microorganisms are held back by the membrane.

Improved devices include a mechanical support that has a reception surface, and the filter unit is mounted on and sealed to said mechanical support so that said membrane and said reception surface form a suction chamber.

A drawback of the above devices is the manner of mounting the filter unit on the mechanical support, which traps and compresses air between the membrane and the reception surface, which can cause the membrane to burst.

Moreover, after the liquid substance has been filtered, residual quantities, which are difficult to evaporate, remain in the suction chamber and moisten the membrane. The microorganisms then tend to diffuse on the culture medium.

A problem that arises and that the present invention seeks to solve is that of providing a mechanical support such that the membrane is protected during mounting and dried after filtration.

To this end, the present invention proposes a mechanical support for a drainage device of a filter unit for microbiological testing of liquid substances, said filter unit being provided with a membrane and adapted to be mounted on said mechanical support so that said membrane faces a reception surface of said mechanical support, which mechanical support is characterized in that it comprises:

a passage one end of which discharges externally of said reception surface and the other end of which discharges onto said reception surface; and selectively operable means for closing said passage, movable between a first position in which they close said passage and a second position in which they open said passage.

Accordingly, one feature of the invention is the provision of a passage that is connected to the interior of the suction chamber and discharges to the exterior of the reception surface, for example to the atmosphere. As a result, when the filter unit is nested over said mechanical support, the selectively operable closure means are driven into said second position to open said passage and air trapped between the membrane and the reception surface, forming the suction chamber, escapes via the passage and is therefore not compressed against the membrane.

As explained in more detail hereinafter, said passage is also kept open when said filter unit is removed, to prevent deterioration of the membrane.

The passage is kept closed during filtration, of course.

In one particularly advantageous embodiment of the invention, said selectively operable closure means comprise a valve adapted to slide in a bore which said passage crosses, said bore discharging onto an external surface portion of said reception head to drive said valve in translation between said first position and said second position.

Accordingly, thanks to this feature, the passage is easily opened or closed by operating the valve from outside the head.

In one particular embodiment of the invention, the mechanical support comprises a suction duct that discharges onto said reception surface to aspirate a liquid substance contained in said filter unit through said membrane.

Accordingly, after all of the liquid substance contained in the filter unit has been filtered and aspirated, because the membrane is relatively impermeable to air, it cannot be dried by the small amount of air that passes through it and is drawn into the suction duct.

The valve is then moved to the second position, to open the passage, and exterior air is aspirated from the outside of the mechanical support, passes through the passage, and then flows into the suction chamber, from which it is evacuated via the suction duct.

As a result, thanks to the passage, the membrane is dried with sterile air coming from the environment of said mechanical support, which is housed in a hood, for example, or in the vicinity of the flame of a Bunsen burner. The resulting dried membrane ensures improved growth of the microorganisms when the membrane is placed on the nutrient medium.

Moreover, because filter supports are difficult to disinfect, not all types of filter unit can be fitted to a particular mechanical support.

To solve this problem, in another particularly advantageous embodiment of the invention, the mechanical support comprises:

a reception head adapted to receive said filter unit and including said reception surface, said passage, said selectively operable closure means, and first connecting means; and a head support including second connecting means, said reception head being adapted to be mounted on said head support so that the first connecting means and the second connecting means cooperate with each other.

Accordingly, not only is the reception head adapted to be replaced by another reception head adapted to receive another type of filter unit, which might have greater volume capacities, for example, or different kinds of filter, but it is also adapted to be sterilized in an autoclave or by immersion in a sterile solution, for example, independently of the other components of the mechanical support. As a result, the reception head is perfectly sterile and contamination of the membrane of a filter unit during a new series of analyses is totally avoided.

Said reception head advantageously has a cylindrically symmetric opening formed in the portion opposite said reception surface to form said first connecting means and said head support has a substantially vertical projecting portion forming said second connecting means and adapted to cooperate with said opening when mounting said reception head on said head support Thus the various reception heads all have an opening of the same size that is identically located in the portion opposite the reception surface so that it can be mounted on the head support, said vertical portions being engaged in said opening.

Said reception head and said head support preferably include keying means for locking said connecting means. Thus the reception head is retained in a fixed position on said head support.

In another particular embodiment of the invention, said reception head has a transverse bore adapted to cooperate with a groove formed around said vertical portion, said transverse bore being adapted to receive key means for forming said keying means.

As a result, the transverse bore which intersects said opening formed in the reception head is adapted to receive key means that are mobile in translation in said bore. The key means are withdrawn from the bore when the reception head is engaged on said head support and are then reinserted to pass through said bore and a portion of the groove in said vertical portion. Thus the reception head is prevented from moving in vertical translation relative to said head support.

It is particularly advantageous if said head support includes a suction branch whose first end is adapted to be connected to said suction duct of said reception head and whose second end is adapted to be connected to a suction pump.

The reception head includes the suction duct through which the liquid substance is aspirated and the head support includes a suction branch adapted to be connected to said suction orifice in order to aspirate the liquid substance by means of the suction pump. Accordingly, the suction orifice of each reception head must be connected to the first end of the suction branch in a substantially sealed manner in order to be able to collect the liquid substance without leaks of air or liquid substance.

Said head support preferably includes a driver device adapted to take up a position opposite said external surface portion and to bear against said valve to drive it in translation into said first position or into said second position.

Accordingly, thanks to this feature, the valve is adapted to be driven from the exterior of the reception head.

According to one advantageous feature, said driver device includes a solenoid whose core is adapted to drive said valve. As a result, the valve is easy to operate with a simple electrical contactor.

In another aspect, the present invention proposes a reception head comprising:

a passage one end of which discharges externally of said reception surface and the other end of which discharges into said chamber;

selectively operable means for closing said passage, movable between a first position in which they close said passage and a second position in which they open said passage;

a cylindrically symmetric opening in the portion opposite said reception surface; and a transverse bore adapted to cooperate with said opening, said transverse bore being adapted to receive key means.

Other features and advantages of the invention will emerge from a reading of the following description of particular embodiments of the invention, which are provided by way of illustrated but nonlimiting example, which description is given with reference to the accompanying drawings, in which.

Figure 1:
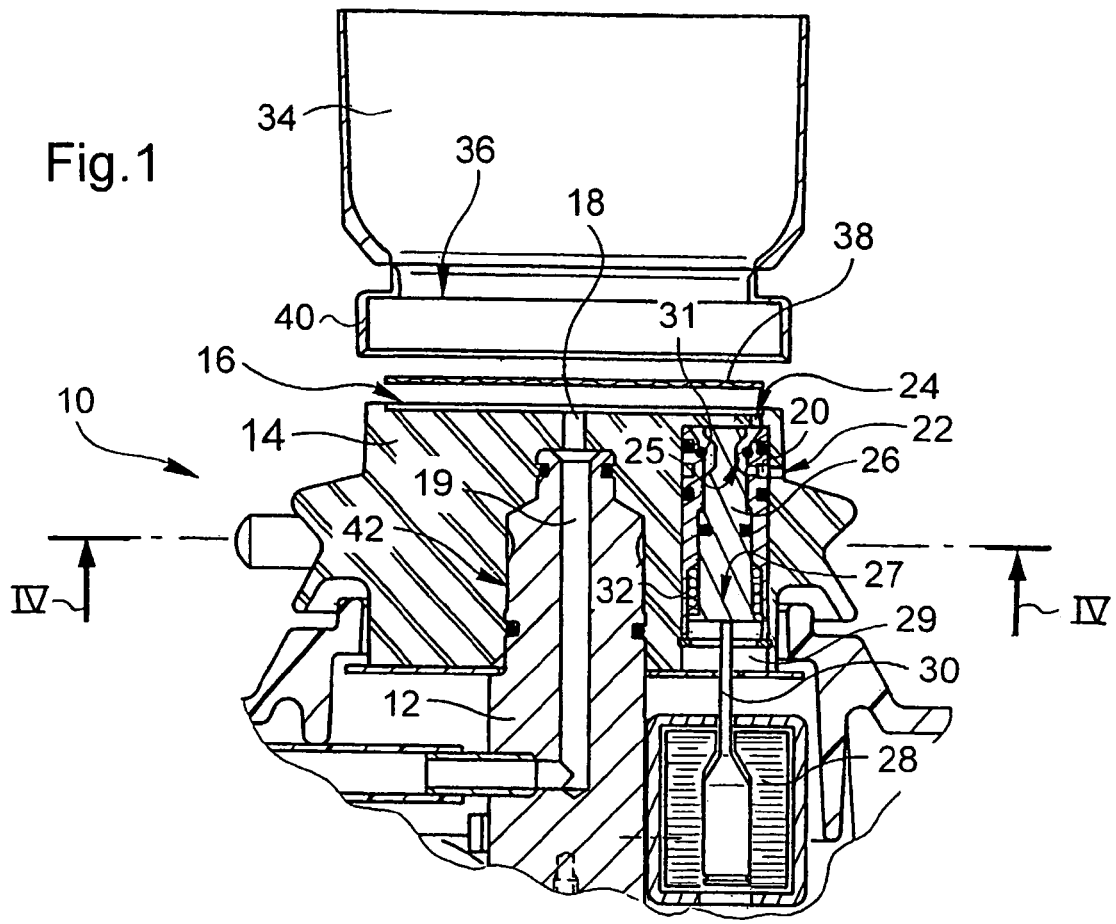
FIG. 1 is a diagrammatic view in vertical section of one particular embodiment of the subject matter of the invention.

FIG. 1 shows a mechanical support 10 according to the invention including a head support 12 and a reception head 14 having a reception surface 16 from which extends an suction duct 18 that is extended by an suction branch 19. The mechanical support 10 shown in vertical section in this figure is a circular cylinder whose axis of symmetry is in the plane of the figure.

Moreover, the reception surface 16 is circular and the suction duct 18 discharges at its center.

The reception head 14 includes a passage 20, one end 22 of which discharges externally of the reception surface 16 and externally of the reception head 14 and the other end 24 of which discharges onto the reception surface 16. In FIG. 1, the passage 20 is closed by a valve 26 in a first position, the valve consisting of a piston in which a groove 25 is provided to form the valve. The valve 26 is mobile in vertical translation in a bore 27 through which said passage passes, said bore 27 discharging at one end onto an external surface portion 29 of the reception head 14. The other end of the bore 27 includes a circular seal projecting from the internal surface of the wall of the bore, which forms a valve seat 31 against which the valve head 26 is bearing in FIG. 1.

The head support 12 includes a driver device 28 formed of a solenoid inside which a core is extended by a punch 30. The driver device 28 is disposed opposite the external surface portion 29 so that the end of the punch 30 is in the bore 27 in the vicinity of the external surface portion, the axis of said punch 30 being substantially parallel to the bore 27.

Figure 2:
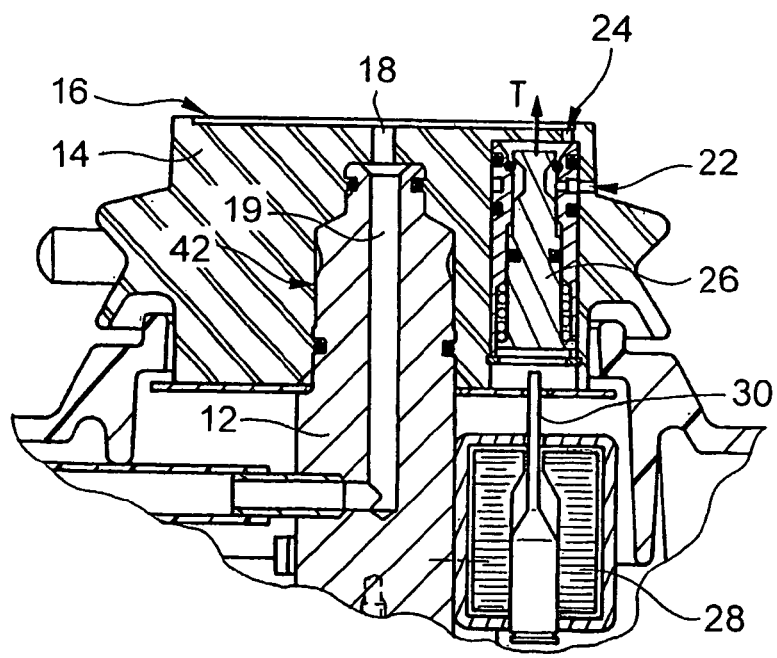
FIG. 2 is a diagrammatic view in vertical section of the subject matter of the invention as shown in FIG. 1 in a particular position.

As a result, when the solenoid 28 is operated, the punch 30 is adapted to drive the valve 26 in the direction of the arrow T to open the passage 20, as shown in FIG. 2.

Moreover, the valve 26 includes a return spring 32 adapted to drive it into the first position when the solenoid 28 is no longer energized, so that the punch 30 returns to its original position.

Refer now to FIG. 2, which shows the mechanical support according to the invention in vertical section and in which can be seen the mechanical support 10 and the driver device 28 whose punch 30 actuates the valve 26 housed in the reception head 14, with the valve in a second position in which the passage 20 is open.

In this second position, the valve head 26 is disengaged from its valve seat 31 with the result that the groove 25 establishes communication between the end 22 of the passage that discharges externally of the reception head 14 and the end 24 of the passage 20 that discharges onto the reception surface 16.

FIG. 1 also shows a filter unit 34 which includes a membrane 36 which is adapted to face the reception surface 16.

The filter unit 34 is adapted to receive a liquid substance to be filtered, the filtrate being aspirated through the membrane 36 and into the suction duct 18.

The membrane 36 is fastened to the filter unit 34 and is separated from the reception surface 16 by a sterile separator 38 consisting of a grid approximately 0.5 mm thick, to prevent it from coming into direct contact with the reception surface 16.

The base 40 of the filter unit 34 and the reception head 14 are substantially frustoconical in shape, for improved centering and to seal the junction between them.

The membrane 36 is relatively impermeable to air, whether dry or moist. Accordingly, when the filter unit 34 is fitted to the reception head 14 and they form a suction chamber between the membrane 36 and the reception surface 16, the air trapped between the two can escape via the open passage 20.

In the same way, a reduced pressure is created in said suction chamber, between the membrane 36 and the reception surface 16, when the filter unit 34 is removed from the reception head 14, and the passage 20 is left open to compensate this reduced pressure.

Furthermore, after the liquid substance has been filtered, residual quantities of filtrates remain in the suction chamber, between the membrane 36 and the reception surface, with the result that the membrane remains moist. The microorganisms tend to diffuse when the moist membrane is placed on the culture medium.

Accordingly, before removing the filter unit 34 from the reception head 14, the passage 20 is opened by moving the valve 26 into the second position, so that sterile external air can be aspirated via the suction duct 18. As a result, the aspirated air tends to dry the suction chamber and therefore the membrane 36.

Moreover, connecting means, not shown, are provided in the perimeter of the end 22 of the passage 20 that discharges externally of the reception head 14 for the connection thereto of a supply of cleaning liquid, for example.

The passage 20 is obviously closed during filtration, on the one hand so that the reduced pressure in the suction chamber is sufficient to aspirate the liquid substance through the membrane 36 and on the other hand to prevent the liquid substance leaking out of the reception head 14.

A particularly advantageous embodiment of the invention in which the reception head 14 is removably mounted on the head support 12 is described next with reference to FIG. 3.

Figure 3:
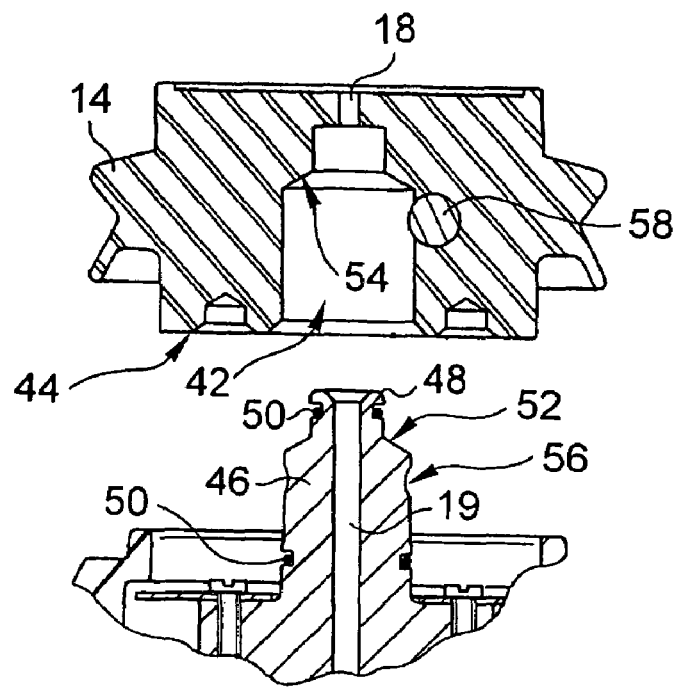
FIG. 3 is a diagrammatic view in vertical section showing an implementation of the subject matter of the inventions-shown in FIG. 1.

FIG. 3 shows the reception head 14 disposed opposite the head support 12, on which it is adapted to bear.

To this end, the reception head 14 has an axial opening 42 in its lower wall 44 adapted to receive a projecting vertical portion 46 of the head support 12. The suction duct 18 discharges directly into the axial opening 42.

The suction branch 19 extends longitudinally in the projecting vertical portion 46 and its first end is intended to be connected, at one end 48 of the projecting vertical part 19, to the suction duct 18 of the reception head 14 when the latter is mounted on the head support 12.

The second end of the suction branch 19 is connected to a vacuum manifold or to a suction pump, not shown, to aspirate the liquid substance contained in the filter unit 34 through the membrane 36.

It is necessary for the connection between the suction branch 19 and the suction duct 18 to be sealed to prevent liquid substance or air leaks. To this end, the projecting vertical portion 46 and the axial opening 42 of the reception head 14 are circular cylinders so that seals 50 can easily be inserted.

The projecting vertical portion 46 also has a first shoulder 52 against which a corresponding second shoulder 54 of the reception head 14 is adapted to bear. As a result the reception head 14 is adapted to be prevented from movement in translation in at least one direction, toward the head support 12.

The projecting vertical portion 46 also has a groove 56 into which key means 58 mounted in said reception head 14 are adapted to be extended.

The key means 58 are described with reference to FIG. 4, which is a view of the reception head 14 shown in FIG. 1 in section taken along the line IV-IV.

Figure 4:
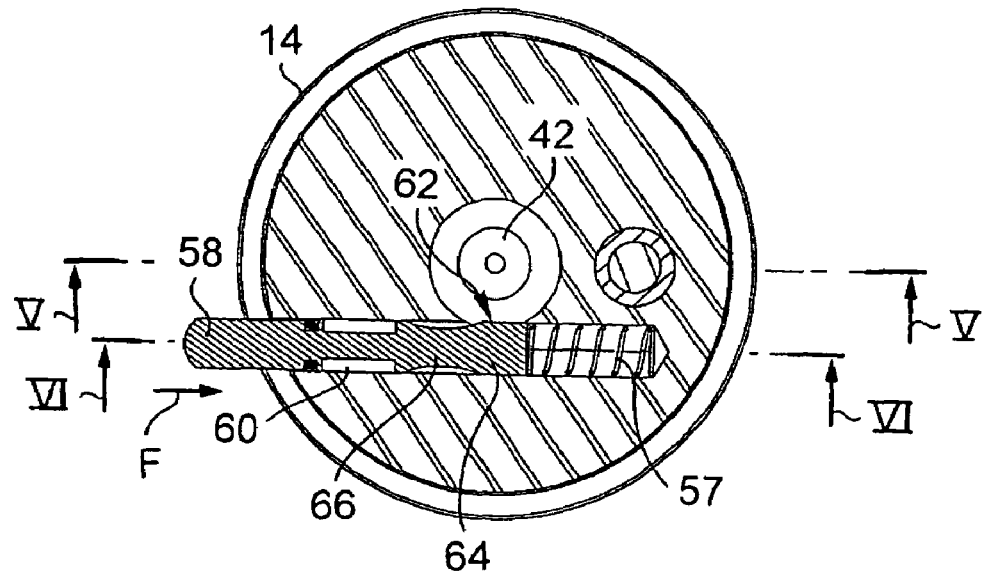
FIG. 4 is a view in section taken along the line IV-IV in FIG 2.

FIG. 4 shows the axial opening 42 and the key means 58, which are mobile in translation in a lateral bore 60 formed in the reception head 14 and a portion 62 of which intersects the axial opening 42.

The key means 58 comprise a rod with a portion 64 whose section is substantially equal to the section of the transverse bore 60 and a portion 66 that forms an elongate groove.

As shown in FIG. 4, the portion 64 of the key means 58 intersects the axial opening 42 with the result that this portion is able to be engaged in the groove 56 of the projecting vertical portion 46 of the head support 12 and thereby connect together the projecting vertical portion 46 and the reception head 14. When the key means 58 are actuated in the direction of the arrow F, a return spring 57 is compressed and the portion 66 is moved opposite the axial opening 42, but does not intersect said axial opening 42, with the result that it is fully open and the reception head 14 can be mounted on the head support 12 or removed therefrom without impediment.

Clearly, when the key means 58 are released, the return spring 57 returns the portion 64 to its original position and movement in translation of the key means 58 in the direction opposite that of the arrow F is prevented by a stop.

A removable reception head 14' in accordance with another embodiment and adapted to be mounted on a head support identical to the head support previously described is described next with reference to FIGS. 5, 6 and 7.

Figure 7:
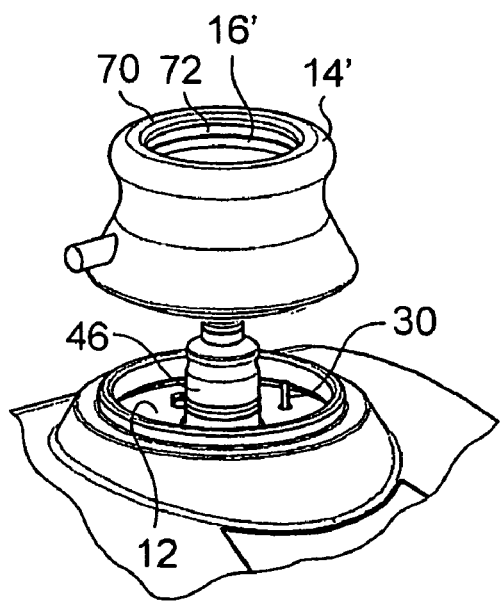
FIG. 7 is a diagrammatic perspective view of said other particular embodiment of the subject matter of the invention.

FIG. 7 shows the reception head 14' positioned above the head support 12 with the projecting vertical portion 46 and the punch 30 of the core of the solenoid 28.

The reception head 14' has a reception surface 16' surrounded by a circular rim 70 against the internal wall of which bears an O-ring 72 lodged in a groove. Accordingly, in this embodiment, a different type of filter unit can be mounted on the reception head 14', the base of said filter unit being nested in the head and bearing against the wall of the circular rim 70 and against the O-ring 72 to provide the seal.

Filter units of the above kind are used when the membrane must be spaced from the reception surface 16' to prevent contamination.

Accordingly, different types of filter unit can be used with the same device including a head support 12, different reception heads being adapted to receive the different filter units.

To this end, the filter heads all comprise the same base adapted to be mounted on the head support 12. As explained with reference to FIG. 6, the reception head 14' includes connecting means identical to those of the reception head 14 shown in FIG. 4.

Figure 6:
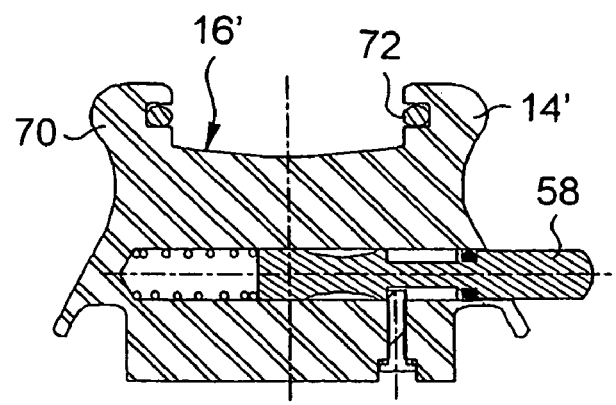
FIG. 6 is a diagrammatic view in vertical section taken along the line VI-VI in FIG. 4 of said other particular embodiment of the invention.

FIG. 6 shows the reception head 14' with its circular rim 70 around the reception surface 16' and its internal wall fitted with the O-ring 72. Furthermore, the reception head 14' comprises key means 58 entirely similar to those of the reception head 14 shown in FIG. 4 and adapted to cooperate with the projecting vertical portion 46 of the head support 12 in the same way.

Figure 5:
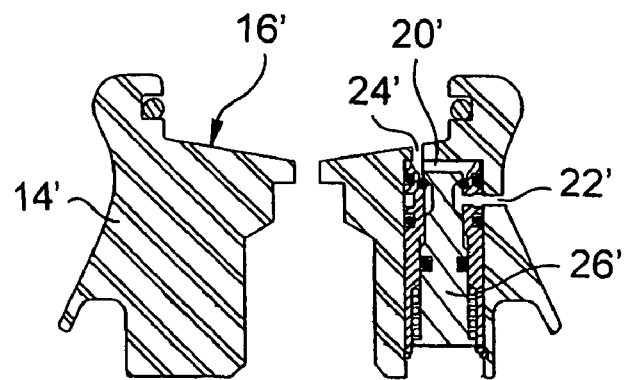
FIG. 5 is a diagrammatic view in vertical section taken along the line V-V in FIG. 4 of a detail of another particular embodiment of the invention.

FIG. 5 is a vertical axial section of the reception head 14' shown in FIG. 7, and shows a passage 20', one end 22' of which discharges externally of the reception surface 16' and externally of the reception head 14', and the other end 24' of which discharges onto the reception surface 16'. In FIG. 5, the passage 20' is closed by a valve 26' in a first position and consisting of a piston similar to that shown in FIG. 1.

The structure and the operation of the valve 26' are identical to those of the valve 26 shown in FIGS. 1 and 2 in order to produce the same result.

The reception heads 14, 14' described hereinabove are made of solid heat-resistant materials that are also resistant to powerful disinfecting agents, so that they can be sterilized at temperatures above 120° C., for example 134° C., and/or by immersion in chlorinated solutions, for example.

The materials used are ideally stainless steels, for example 316L stainless steel, or plastics materials, for example PEEK.

The seals are made from elastomer type plastics materials, for example polyurethane, which resist heat treatment and sterile solutions.

The present invention is in no way limited to the embodiments described and shown, which the person skilled in the art will know how to modify within the spirit of the invention.

The invention claimed is:

1. A mechanical support for a drainage device of a filter unit adapted to be mounted on said mechanical support wherein said mechanical support comprises: (1) a reception head including a reception surface and an external surface portion, wherein said reception head is adapted to receive said filter unit; (2) a passage, one end of which discharges externally of said reception surface facing a membrane provided in the filter unit and the other end of which discharges onto said reception surface; (3) selectively operable closure means, movable between a first position to close said passage and a second position to open said passage, wherein said selectively operable means comprises a valve adapted to slide in a bore which discharges onto said external surface portion of said reception head; and (4) a driver device adapted to bear against said valve to drive it in translation into said first position or into said second position, wherein said passage is opened or closed by operating said valve from outside said reception head.

2. The mechanical support according to claim 1, wherein said support further comprises a suction duct that discharges onto said reception surface, thereby to aspirate a liquid substance contained in said filter unit through said membrane.

3. The mechanical support according to claim 1, wherein said mechanical support further comprises first connecting means and a head support including second connecting means, said reception head being adapted to be mounted on said head support so that the first connecting means and the second connecting means cooperate with each other.

4. The mechanical support according to claim 3, wherein said first connecting means is formed by a cylindrically symmetric opening in said reception head formed in a portion opposite said reception surface and said second connecting means is formed by a substantially vertical projecting portion in said head support and is adapted to cooperate with said opening when mounting said reception head on said head support.

5. The mechanical support according to claim 3, wherein said reception head and said head support include keying means for locking said first and second connecting means.

6. The mechanical support according to claim 3, wherein said reception head has a transverse bore adapted to cooperate with a groove formed around said vertical projecting portion, said transverse bore being adapted to receive key means comprising a rod for forming keying means.

7. The mechanical support according to claim 2, wherein said head support includes a suction branch having a first end adapted to be connected to said suction duct of said reception head and a second end adapted to be connected to a suction pump.

8. The mechanical support according to claim 1, wherein said driver device is adapted to take up a position opposite said external surface portion.

9. The mechanical support according to claim 8 wherein said driver device includes a solenoid whose core is adapted to drive said valve.

10. The mechanical support of claim 6, wherein the rod comprises one portion comprising a section substantially equal to the section of said transverse bore and a second portion comprising an elongate groove.

11. A reception head comprising a reception surface and adapted to receive a filter unit, wherein said reception head comprises: (1) a passage, one end of which discharges externally of said reception surface and the other end of which discharges internally of said reception surface; (2) selectively operable means for closing said passage, movable between a first position to close said passage and a second position to open said passage, wherein said selectively operable means comprises a valve adapted to slide in a bore which discharges onto an external surface portion of said reception head and wherein the valve is operated from outside of said reception head; (3) a cylindrically symmetric opening formed in a portion opposite said reception surface; and (4) a transverse bore adapted to cooperate with said opening, said transverse bore being adapted to receive key means comprising a rod for forming keying means.

12. The mechanical support of claim 11, wherein the rod comprises one portion comprising a section substantially equal to the section of said transverse bore and a second portion comprising an elongate groove.

13. A mechanical support for a drainage device of a filter unit adapted to be mounted on said mechanical support wherein said mechanical support comprises: (1) a passage, one end of which discharges externally of a reception surface facing a membrane provided in the filter unit and the other end of which discharges onto said reception surface; (2) selectively operable closure means, movable between a first position to close said passage and a second position to open said passage, wherein said selectively operable means comprises a valve adapted to slide in a bore which discharges onto an external surface portion of a reception head to drive said valve in translation between said first position and said second position; and (3) a reception head comprising a transverse bore adapted to cooperate with a groove formed around said vertical projecting portion, said transverse bore being adapted to receive key means comprising a rod for forming keying means.

* * * * *